(12) United States Patent
Xie et al.

(10) Patent No.: US 12,706,204 B2
(45) Date of Patent: Aug. 11, 2026

(54) METHODS AND SYSTEMS FOR MEDICAL DATA PROCESSING

(71) Applicant: SHANGHAI UNITED IMAGING HEALTHCARE CO., LTD., Shanghai (CN)

(72) Inventors: Huifang Xie, Shanghai (CN); Yun Dong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 38 days.

(21) Appl. No.: 18/823,652

(22) Filed: Sep. 3, 2024

(65) Prior Publication Data

US 2025/0118419 A1 Apr. 10, 2025

(30) Foreign Application Priority Data

Oct. 7, 2023 (CN) ......................... 202311288119.9

(51) Int. Cl.
*G16H 30/40* (2018.01)
*G06N 3/045* (2023.01)
*G06N 3/088* (2023.01)

(52) U.S. Cl.
CPC ............. *G16H 30/40* (2018.01); *G06N 3/045* (2023.01); *G06N 3/088* (2013.01)

(58) Field of Classification Search
CPC ......... G16H 30/40; G06N 3/045; G06N 3/088
See application file for complete search history.

(56) References Cited

U.S. PATENT DOCUMENTS

2023/0067841 A1* 3/2023 Saharia .................. G06N 3/047

OTHER PUBLICATIONS

Ho et al., Denoising Diffusion Probabilistic Models, 34th Conference on Neural Information Processing Systems (Year: 2020).*
Chung et al., MR Image Denoising and Super-Resolution Using Regularized Reverse Diffusion, 42(4) IEEE Transactions on Medical Imaging (Apr. 2023) (Year: 2023).*

* cited by examiner

*Primary Examiner* — Jordan L Jackson
(74) *Attorney, Agent, or Firm* — METIS IP LLC

(57) ABSTRACT

A method for generating a medical data processing network. The method is performed by a medical imaging system, and the method includes: in response to receiving a training instruction, obtaining first medical data, the training instruction being triggered by a user on an application interface of a processing device of the medical imaging system; obtaining a second network by training a first network based on the first medical data, the training including an unsupervised training; generating a test result by inputting second medical data into the second network, the second medical data including a test sample set; determining an evaluation result of a performance of the second network based on the test result; and in response to the evaluation result indicating that the performance of the second network satisfies a requirement, storing a parameter of the second network.

20 Claims, 9 Drawing Sheets

METHODS AND SYSTEMS FOR MEDICAL DATA PROCESSING

CROSS-REFERENCE TO RELATED APPLICATION

This application claims priority to Chinese application No. 202311288119.9 filed on Oct. 7, 2023, the entire contents of which are incorporated herein by reference.

TECHNICAL FIELD

The present disclosure relates to the field of medical technology, and in particular to methods and systems for generating a medical data processing network and utilizing the network for medical data processing.

BACKGROUND

With the rapid development of neural network technology, the use of a neural network is becoming more and more widespread in a medical field. Often, a healthcare organization, such as a hospital, directly processes medical data using an already trained neural network provided by a supplier. However, for purposes such as protecting a user privacy, the healthcare organization has a strict data control, and the supplier is unable to obtain the medical data timely, resulting in a poor generalization ability (an ability to adapt or generalize on unexposed or less-exposed data) of the neural network provided by supplier.

It is therefore desirable to provide methods and systems for generating a medical data processing network to improve the generalization ability of the neural network for processing the medical data, as well as to utilize the network for medical data processing to improve an accuracy of the medical data processing.

SUMMARY

One or more embodiments of the present disclosure provide a method for generating a medical data processing network. The method is performed by a medical imaging system, and the method includes: in response to receiving a training instruction, obtaining first medical data, the training instruction being triggered by a user on an application interface of a processing device of the medical imaging system; obtaining a second network by training a first network based on the first medical data, the training including an unsupervised training; generating a test result by inputting second medical data into the second network, the second medical data including a test sample set; determining an evaluation result of a performance of the second network based on the test result; and in response to the evaluation result indicating that the performance of the second network satisfies a requirement, storing a parameter of the second network.

One of the embodiments of the present disclosure provides medical imaging system including an imaging device, a processing device, a storage device, one or more terminals, and a network. The processing device is configured to: in response to receiving a training instruction, obtain first medical data, the training instruction being triggered by a user on an application interface of a processing device of the medical imaging system; obtain a second network by training a first network based on the first medical data, the training including an unsupervised training; generate a test result by inputting second medical data into the second network, the second medical data including a test sample set; determine an evaluation result of a performance of the second network based on the test result; and in response to the evaluation result indicating that the performance of the second network satisfies a requirement, store a parameter of the second network.

One or more embodiments of the present disclosure provide method for processing medical data. The method is performed by a processing device including at least one processor and at least one storage device, and the method includes: obtaining medical data to be processed; in response to receiving a selection instruction, obtaining a basic network model and a target parameter, the selection instruction being triggered by a user on an application interface of the processing device, and the selection instruction being configured to select the target parameter from a plurality of parameters and the basic network model from a plurality of network models; generating a target network model based on the target parameter and the basic network model; and obtaining a processing result by inputting the medical data to be processed into the target network model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
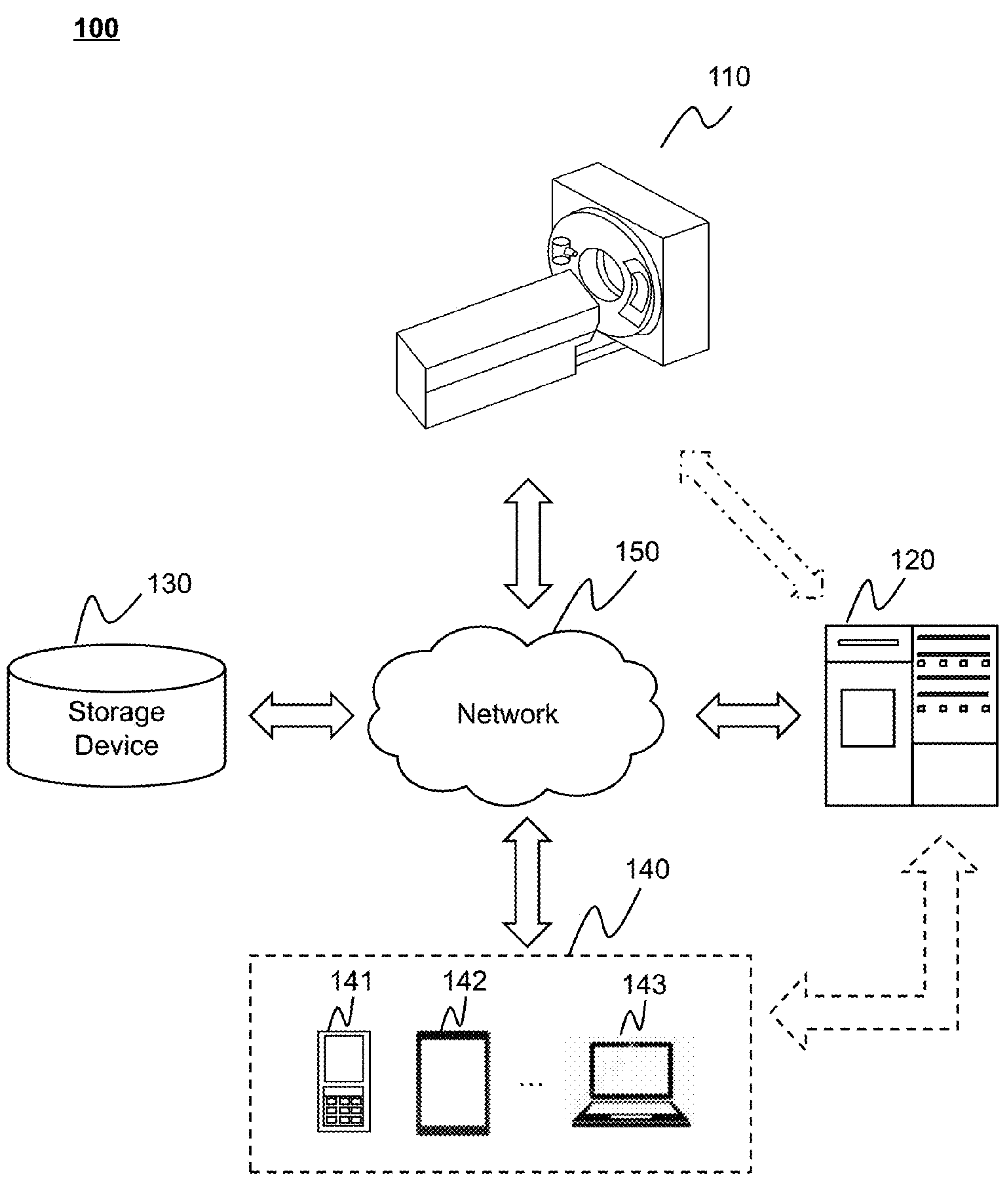
FIG. 1 is a schematic diagram illustrating an exemplary medical imaging system according to some embodiments of the present disclosure.

In the following detailed description, numerous specific details may be set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments may be readily apparent to those skilled in the art, and the general principles defined herein may be applied to other embodiments and applications without departing from the spirit and scope of the present disclosure. Thus, the present disclosure may be not limited to the embodiments shown, but to be accorded the widest scope consistent with the claims.

The terminology used herein may be for the purpose of describing particular example embodiments only and may be not intended to be limiting. As used herein, the singular forms "a," "an," and "they" may be intended to include the plural forms as well, unless the context clearly indicates otherwise. It may be understood that the terms "system," "unit," "module," and/or "block" used herein are one method to distinguish different components, elements, parts, sections or assemblies of different levels in ascending order. However, the terms may be displaced by another expression if they achieve the same purpose.

The modules (or units, blocks, units) described in the present disclosure may be implemented as software and/or hardware modules and may be stored in any type of non-transitory computer-readable medium or other storage devices. In some embodiments, a software module may be compiled and linked into an executable program. It may be appreciated that software modules may be callable from other modules or from themselves, and/or may be invoked in response to detected events or interrupts. Software modules configured for execution on processing devices may be provided on a computer readable medium or as a digital download (and can be originally stored in a compressed or installable format that requires installation, decompression, or decryption prior to execution). Such software code may be stored, partially or fully, on a memory device of the executing processing device, for execution by the processing device. Software instructions may be embedded in a firmware, such as an EPROM. It may be further appreciated that hardware modules (e.g., circuits) may be included in connected or coupled logic units, such as gates and flip-flops, and/or may be included in programmable units, such as programmable gate arrays or processors. The modules or processing device functionality described herein may be preferably implemented as hardware modules, but may be software modules as well. In general, the modules described herein refer to logical modules that may be combined with other modules or divided into units despite their physical organization or storage.

Certain terminology has been used to describe embodiments of the present disclosure. For example, the terms "one embodiment," "an embodiment," and/or "some embodiments" may mean that a particular feature, structure or characteristic described in connection with the embodiment is in at least one embodiment of the present disclosure. Therefore, it is emphasized and should be appreciated that two or more references to "an embodiment" or "one embodiment" or "an alternative embodiment" in various portions of the present disclosure may not necessarily all referring to the same embodiment. Furthermore, the particular features, structures or characteristics may be combined as suitable in one or more embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings may be for the purpose of illustration and description only and may be not intended to limit the scope of the present disclosure.

The flowcharts used in the present disclosure may illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

In a clinical use of a neural network to process medical data, when a new clinical scenario arises, the medical data may not be delivered to a supplier timely, e.g., the new clinical scenario may include an application of some new medicine and an establishment of a new workflow in a hospital, resulting in an existing neural network being unable to adapt to the new clinical scenario. Currently, the neural network for processing the medical data usually uses a supervised training, i.e., using labeled training data sets to train neural networks, which requires a great amount of training data, and has a high hardware requirement, resulting in a high training cost. In addition, for purposes such as protecting a user privacy, the medical data is tightly controlled, and the hospital and other healthcare organizations may not be able to provide the medical data directly to an outside world, making it difficult for the supplier of the neural network to improve, through comprehensive data, a generalization ability of the neural network.

Some embodiments of the present disclosure provide a method and system for generating a medical data processing network. The method is performed by a medical imaging system. The method includes in response to receiving a training instruction, obtaining first medical data. The training instruction is triggered by a user on an application interface of a processing device of a medical imaging system. The method includes obtaining a second network by training a first network based on the first medical data. The training includes an unsupervised training. The method includes generating a test result by inputting second medical data into the second network. The second medical data includes a test sample set. The method includes determining an evaluation result of a performance of the second network based on the test result. The method further includes in response to the evaluation result indicating that the performance of the second network satisfies a requirement, storing a parameter of the second network.

According to some embodiments of the present disclosure, the training of the medical data processing network does not need to go through an external supplier, and may be performed directly on the medical imaging system, so that a source of data for training the network is unlimited, and new medical data (e.g., a new clinical scenario) may be used timely, which improves the generalization ability of the network, and makes the network to be able to adapt to new clinical scenarios timely. Further, according to some embodiments of the present disclosure, the network may be tested based on the second medical data, and the performance of the network may be evaluated by the test result. In this way, a parameter of the generated network may be more accurate and the generated network may be more reliable and practical. In addition, the network is trained using the unsupervised training, which eliminates a need to obtain a great count of training samples (e.g., the first medical data) and does not require labeling the training samples, resulting in a low hardware requirement and greatly saving training costs.

FIG. 1 is a schematic diagram illustrating an exemplary medical imaging system 100 according to some embodiments of the present disclosure. As shown in FIG. 1, the medical imaging system 100 may include an imaging device 110, a processing device 120, a storage device 130, one or more terminals 140, and a network 150. In some embodiments, the imaging device 110, the processing device 120, the storage device 130, and/or the terminal 140 may be connected to and/or communicate with each other via a wireless connection, a wired connection, or a combination thereof.

The imaging device 110 may be configured to scan a target subject (or a portion of the target subject) to obtain medical image data associated with the target subject. The medical image data relating to the target subject may be used for generating a medical image (e.g., a computed tomography (CT) image, a magnetic resonance (MR) image, a positron emission tomography (PET) image, etc.) of the target subject. The medical image may illustrate an internal structure and a health condition of the target subject. In some embodiments, the imaging device 110 may include a single-modality scanner and/or a multi-modality scanner. The single modality scanner may include, for example, a CT scanner, a MR scanner, a PET scanner, etc. The multi-modality scanner may include, for example, a PET-X-ray imaging (PET-X-ray) scanner, a PET-computed tomography (PET-CT) scanner, etc. It may be noted that the imaging device 110 described below is merely provided for illustration purposes, and not intended to limit the scope of the present disclosure.

In some embodiments, the processing device 120 may be a single server or a server group. The server group may be centralized or distributed. The processing device 120 may process data and/or information obtained from the imaging device 110, the storage device 130, and/or the terminal 140. For example, the processing device 120 may obtain first medical data in response to receiving a training instruction. The training instruction is triggered by a user on an application interface of the processing device 120. The processing device 120 may obtain a second network by training a first network based on the first medical data. The training includes an unsupervised training. The processing device 120 may input second medical data into the second network to generate a test result. The second medical data may include a test sample set. The processing device 120 may determine an evaluation result of a performance of the second network based on the test result. The processing device 120 may further stored a parameter of the second network in response to the evaluation result indicating that the performance of the second network satisfies a requirement.

In some embodiments, the processing device 120 may be local or remote from the medical imaging system 100. In some embodiments, the processing device 120 may be implemented on a cloud platform. In some embodiments, the processing device 120 or a portion of the processing device 120 may be integrated into the imaging device 110 and/or the terminal 140. It may be noted that the processing device 120 in the present disclosure may include one or more processors. Thus operations and/or steps performed by one processor may also be jointly or separately performed by a plurality of processors.

The storage device 130 may store data, instructions, and/or any other information. In some embodiments, the storage device 130 may store data obtained from the imaging device 110, the processing device 120, and/or the terminal 140. In some embodiments, the storage device 130 may store the data and/or instructions performed or used by the processing device 120 to perform the exemplary method described in the present disclosure. In some embodiments, the storage device 130 may include a mass storage device, a removable storage device, a volatile read-and-write memory, a read-only memory (ROM), etc., or a combination thereof. In some embodiments, the storage device 130 may be implemented on the cloud platform. In some embodiments, the storage device 130 may be a portion of the imaging device 110, the processing device 120, and/or the terminal 140.

The terminal 140 may be configured to enable a user interaction between a user and the medical imaging system 100. In some embodiments, the terminal 140 may be connected to and/or communicate with the imaging device 110, the processing device 120, and/or the storage device 130. Merely by way of example, an application interface of the processing device 120 may display through the terminal 140, the user may issue the instructions through the terminal 140. For example, the user may trigger various operation instructions such as a training instruction by clicking a button and a menu, etc. on the application interface. In some embodiments, the terminal 140 may include a mobile device 141, a tablet computer 142, a laptop computer 143, etc., or a combination thereof. In some embodiments, the terminal 140 may be a portion of the processing device 120 and/or the imaging device 110.

The network 150 may include any suitable network that facilitates an exchange of information and/or data for the medical imaging system 100. In some embodiments, one or more components of the medical imaging system 100 (e.g., the imaging device 110, the processing device 120, the storage device 130, the terminal 140, etc.) may communicate the information and/or data with one or more other components of the medical imaging system 100 via the network 150.

It should be noted that the above description is intended to be illustrative, and not to limit the scope of the present disclosure. Many alternatives, modifications, and variations are apparent to those skilled in the art. The features, structures, methods, and characteristics of the exemplary embodiments described herein may be combined in various ways to obtain additional and/or alternative exemplary embodiments. In some embodiments, the medical imaging system 100 may include one or more additional components and/or one or more components described above may be omitted.

Additionally or alternatively, two or more components of the medical imaging system 100 may be integrated into a single component. For example, the processing device 120 may be integrated into the imaging device 110. As another example, a component of the medical imaging system 100 may be replaced by another component that implements the same function. However, those variations and modifications do not depart from the scope of the present disclosure.

Figure 2:
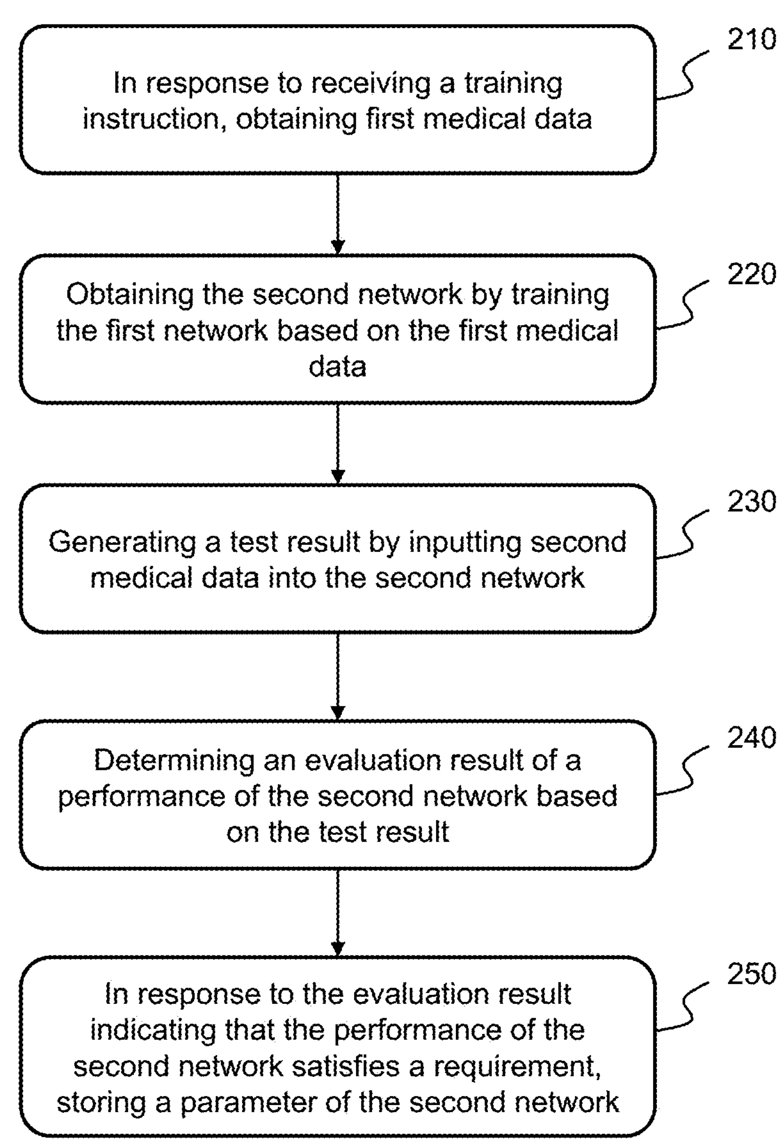
FIG. 2 is a flowchart illustrating an exemplary process for generating a medical data processing network according to some embodiments of the present disclosure.

FIG. 2 is a flowchart illustrating an exemplary process for generating a medical data processing network according to some embodiments of the present disclosure. In some embodiments, a process 200 may be performed by the medical imaging system 100 (e.g., a parameter generation module 950 of the processing device 120). For example, the process 200 may be implemented as a group of instructions (e.g., an application) stored in a storage device (e.g., the storage device 130 illustrated in FIG. 1). In some embodiments, the processing device 120 of the medical imaging system 100 and/or one or more modules of the processing device 120 shown in FIG. 9 may perform the group of instructions and may accordingly be directed to perform the process 200.

In step 210, in response to receiving a training instruction, first medical data is obtained. In some embodiments, the step 210 may be performed by an obtaining unit 951 illustrated in FIG. 9.

In some embodiments, a user may trigger a training instruction by manipulating a control component on an application interface of the processing device (e.g., the processing device 120). The training instruction refers to an instruction for training a first network to obtain a second network whose performance satisfies a requirement. The user may be a staff member of a medical organization such as a hospital, e.g., a doctor, a technician, etc. The first network (also referred to as an initial medical data processing network) is a network whose performance does not satisfy a user's demand. For example, the first network is an untrained initial network. As another example, the first network is an initially trained intermediate network. The first network may be obtained from a supplier end (e.g., a supply's server).

The second network (also referred to as a trained medical data processing network or a target network model) refers to a trained network whose performance satisfies the user's demand. In some embodiments, the first network or the second network may include a machine learning model. For example, the first network or the second network includes a deep learning network such as a convolutional neural network (CNN), a deep belief network (DBN), a recurrent neural network (RNN), a long short-term memory (LSTM), etc.

The application interface refers to an interface of the processing device for display application software related to the medical data processing. The application interface is an interface communicatively connected to the processing device, such as an interface of the processing device itself, an interface of a terminal (e.g., the terminal 140) communicatively connected to the processing device. On the application interface, various control components may be displayed. Through the various control components, various instructions may be triggered. For example, the training instruction may be triggered through the control component corresponding to the training instruction.

In some embodiments, the terminal may include the application software for training the first network, and when required, the user clicks on an icon of the application software, and the terminal enters the application interface in response to the click operation. A start training control component is displayed on the application interface, and the user triggers the start training control component (by the click operation or a slide operation, etc.), the terminal generates a training instruction in response to the trigger and sends the training instruction to the processing device, and the processing device obtains the first medical data based on the training instruction.

In some embodiments, the training control component of the first network is displayed on the application interface of the terminal, which is triggered by the click operation or the slide operation, etc. The user triggers the training control component on the application interface, and the terminal generates the training instruction in response to the triggering and sends the training instruction to the processing device, and the processing device obtains the first medical data based on the training instruction.

The first medical data refers to a training sample used to train the first network. The first medical data may include raw scan data, a medical image, other medical information (e.g., a diagnostic report, etc.), etc. In some embodiments, the processing device may obtain the first medical data in various ways. For example, the first medical data may be pre-stored in a storage device (e.g., the storage device 130), and the processing device may obtain the first medical data from the storage device based on the training instruction. As another example, the first medical data may be input by the user, and the processing device may send a reminding message to the user based on the training instruction to remind the user to input the first medical data. As yet another example, the processing device may obtain, directly from a medical imaging device (e.g., the imaging device 110) associated with the medical data processing network, scan data as the first medical data.

In some embodiments, in response to receiving the training instruction, the processing device may obtain the first medical data based on the initial medical data. For descriptions of how to obtain the first medical data based on the initial medical data, please refer to FIG. 4.

According to the embodiments in the present disclosure, the user may obtain the first medical data in real time in case of changes in the clinical application environment (e.g., the application of new medicines, the establishment of new workflows, etc.), and then the first medical data is used to train the first network, so that the trained first network (i.e., the second network) has a stronger generalization ability, and is able to adapted to a state of hospitals where the medical data is decentralized and the clinical application scenarios are diversified.

In step 220, the second network is obtained by training the first network based on the first medical data. In some embodiments, step 220 may be performed by a training unit 952 illustrated in FIG. 9.

In some embodiments, the processing device 120 may obtain the training sample of the first network based on the first medical data, and train the first network to obtain the second network. The training of the first network includes an unsupervised training. Specifically, during the training process, an input of the first network may include the first medical data, and an output of the first network may include processed first medical data. The processing may include at least one of an image reconstruction, a noise reduction, an artifact removal, an image registration, an image segmentation, etc. For example, the input of the first network may be a medical image and the output of the first network may be a processed medical image (e.g., a noise reduced medical image, an artifact removed medical image, a registered medical image, a segmented medical image). As another example, the input of the first network may be raw scan data of the medical imaging device, and the first network may perform the image reconstruction on the raw scan data, and then further process (e.g., the noise reduction, the artifact removal, the image registration, the image segmentation) the reconstructed image to output the processed medical image.

Figure 3:
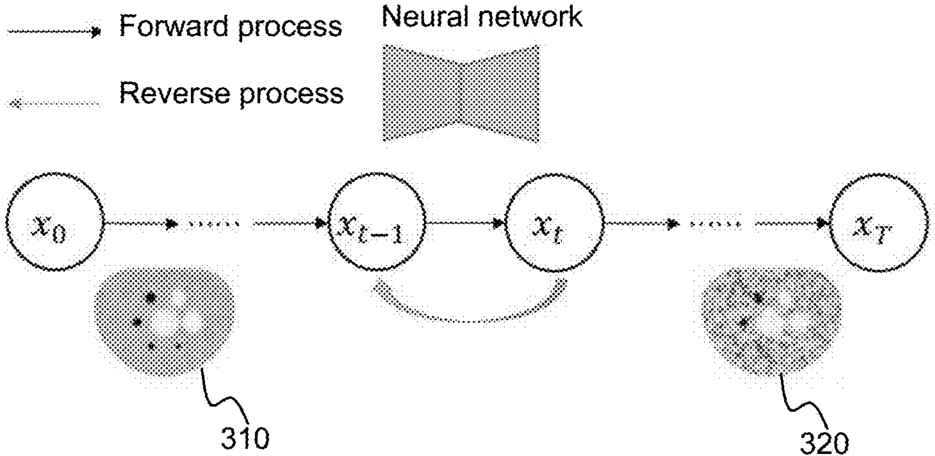
FIG. 3 is a schematic diagram illustrating an exemplary diffusion model according to some embodiments of the present disclosure.

The first network may be implemented based on a diffusion model. FIG. 3 is a schematic diagram illustrating an exemplary diffusion model according to some embodiments of the present disclosure. As shown in FIG. 3, the diffusion model is a neural network, and a processing process of a medical image by the Diffusion model may include a forward process and a reverse process. The forward process includes a process of $x_0 \rightarrow \ldots \rightarrow x_{t-1} \rightarrow x_t \rightarrow \ldots \rightarrow x_T$, t>2, T>t, where $x_0, \ldots, x_{t-1}, x_t, \ldots$, and $x_T$ are medical images. From $x_0$ to $x_T$, the quality of medical images tends to decrease, e.g., there are more noises and more artifacts, etc. From FIG. 3, it may be seen that $x_0$ corresponds to an image 310 with very little noise and a high image quality, and $x_T$ corresponds to an image 320 with more noises and a poorer image quality. The reverse process is an inverse process of the forward process, and the reverse process includes a process of $x_0 \leftarrow \ldots \leftarrow x_t\text{-}1 \leftarrow x_t \leftarrow \ldots \leftarrow x_T$. From $x_T$ to $x_0$, the quality of the medical image tends to increase, e.g., the noise is reduced, the artifacts are reduced, etc. As may be seen from FIG. 3, the inverse process is actually a process of noise reduction, artifact removal, and other operations on the medical image.

In some embodiments, the processing device may select a first network from a plurality of candidate networks based on a training object specified in a training instruction. The plurality of candidate networks may be initially trained networks or networks that are not initially trained. The training object refers to a network to be trained that is explicitly specified by a user in the training instruction. For example, the plurality of candidate networks are stored in a medical imaging system (e.g., the medical imaging system 100), including a network 1, a network 2, and a network 3, and the user specifies the training object as network 1 in the training instruction, then the processing device determines network 1 as the first network. In some embodiments, instead of using an initially trained network already stored in the medical imaging system, the processing device 120 may create a new network to train the new network.

In some embodiments, the processing device may train the first network continuously. For example, the processing device 120 may train the first network continuously for 24 hours per day. In some embodiments, the processing device 120 may train the first network at a preset training frequency. By training the first network continuously or at the preset training frequency, the network training frequency may be adjusted according to the specific requirement of the user to satisfy diversified requirements of the user. For example, the user may adapt to new clinical scenarios in real time through the continuous training. As another example, the user may set the training frequency to reduce a resource consumption.

In some embodiments, the preset training frequency may be determined based on imaging data (e.g., a volume of imaging data) of a medical imaging device (e.g., the imaging device 110) associated with a medical data processing network. For example, the preset training frequency may be related to a daily scanning volume of the medical imaging device associated with the medical data processing network. The daily scanning volume refers to the volume of scan data generated by the medical imaging device per day. The greater the daily scanning volume, the higher the training frequency; the smaller the daily scanning volume, the lower the training frequency. Dynamically adjusting the training frequency according to the daily scanning volume may balance resources consumed by training with a training quality, so as to maintain a good training quality without wasting resources.

In some embodiments, the preset training frequency may be determined using a vector database based on the imaging data of the medical imaging device associated with the medical data processing network. The vector database refers to a database system specialized for storing, managing, and retrieving high-dimensional vector data, which is widely used in the field of machine learning. Specifically, the vector database may include reference vectors (vectors of the imaging data corresponding to the plurality of daily scanning volumes) and reference training frequencies corresponding to the reference vectors. The processing device 120 may construct a vector database based on vectors of the imaging data corresponding to the plurality of daily scans of the medical imaging device and the training frequencies corresponding to the vectors. When applied, the processing device 120 may construct a target feature vector based on the obtained daily scanning volume, and match the at least one reference vector in the vector database that satisfies a preset condition based on the target feature vector. The preset condition may be that a distance between the target feature vector and the reference vector is less than a distance threshold. Merely by way of example, the vector distance may be a Euclidean distance, a cosine distance, etc. The processing device 120 may take the average value of the training frequencies corresponding to the at least one reference vector as the preset training frequency.

In some embodiments, a preset training frequency may be determined, based on the imaging data of the medical imaging device associated with the medical data processing network, by using a machine learning model. For example, the processing device 120 may input scan data corresponding to the daily scanning volume of the medical imaging device into the machine learning model to obtain an output training frequency. The machine learning model may include a deep learning model, such as, for example, a CNN, RNN, or LSTM, etc. Training samples of the machine learning model may be obtained from a great volume of historical scan data. Labels corresponding to the training samples may be optimal training frequencies corresponding to the training samples. The optimal training frequency may be obtained by actual testing, from historical data, etc. The processing device 120 may train the machine learning model based on the training samples and the labels by supervised training.

Merely by way of example, the processing device 120 may obtain the optimal training frequency through actual testing. The processing device 120 may obtain a plurality of sets each of which includes daily scanning data samples. The daily scanning data samples in each set correspond to different daily scanning volumes. For each of these sets, the processing device 120 may test the effect of different training frequencies on the image quality through a series of experiments. Each experiment processes images corresponding to the daily scan data sample using a non-repeating training frequency and evaluates the image quality after processing. For each experiment, the processing device 120 may quantitatively assess the quality of the processed images using various image quality assessment metrics. For example, these assessment metrics may include a sharpness, a contrast, a noise level, a detail retention, etc. The processing device 120 may select the training frequency that performs optimally on the evaluation metrics as the corresponding label for the daily scanning volume corresponding to the daily scan data samples in this set. For example, suppose there are 5 different combinatorial network configurations (Config1, Config2, . . . , Config5), each with a different training frequency. These five configurations are then used separately to process the same set A and the image quality assessment metrics are calculated for each configuration, assuming a sharpness score of (80, 85, 90, 75, 82). The processing device 120 may determine Config3 (with a sharpness score of 90) as the optimally performed configuration, and record Config3 as the corresponding label for the daily scanning volume corresponding to the daily scan data samples in set A.

Merely by way of example, the processing device 120 may collect the imaging data under different parameters and conditions through the medical imaging device associated with the medical data processing network. The processing device 120 may preprocess collected data to extract a plurality of daily scanning volumes as a plurality of training samples. The processing device 120 may assign the labels to each training sample based on an actual imaging result or historical experience.

In some embodiments, the training frequencies corresponding to a plurality of medical centers associated with the medical data processing network may be the same, i.e., the processing device 120 may synchronize or share the training frequencies across the plurality of medical centers. For example, the processing device 120 may update (e.g., increase or decrease) the training frequency of medical center B based on the training frequency of the medical center A. The update may be such that the training frequency of the medical center B is the same as the training frequency of the medical center A.

In some embodiments, the unsupervised training for the first network may include a self supervised training. The self supervised training refers to generating training data and labels based on existing data, and using the generated training data and labels to train a model. In some embodiments, the processing device 120 may automatically generate the training data and the labels based on first medical data. For example, when raw scan data of the medical imaging device is used as the training sample, the processing device 120 may automatically perform an image reconstruction on the raw scan data, and use the obtained reconstructed image as a label corresponding to that training sample. As another example, the processing device 120 may automatically perform the image reconstruction on the raw scan data, and use the reconstructed image obtained as the training sample. Further, the processing device 120 may process the reconstructed image (e.g., the noise reduction or the artifact removal, etc.) and use the processed image as the label corresponding to the training sample. As yet another example, the processing device 120 may use the reconstructed image as the label and process the reconstructed image (e.g., add noise or artifacts, etc.), and use the processed image as the training sample corresponding to that label.

In some embodiments, the processing device 120 may train the first network based on the training data and the labels to obtain the second network. For example, when the reconstructed image is used as the training sample, the processing device 120 may input the reconstructed image into the first network to obtain an output image, and iteratively update a parameter (also referred to as a model parameter or a network parameter) of the first network based on the output image and the label (i.e., the processed image) corresponding to the reconstructed image. By automatically generating the training data and the labels based on the first medical data, thereby training the first network to obtain the second network, there is no need to obtain a great count of training samples and to label the training samples manually, which has a low hardware requirement, and is able to greatly save training costs. For more contents on how to train the first network based on the first medical data, please refer to FIG. 5.

In step 230, a test result is generated by inputting second medical data into the second network. In some embodiments, step 230 may be performed by a testing unit 953 illustrated in FIG. 9.

The second medical data refers to data used to perform tests on the medical data processing network. For example, the second medical data may include the raw scan data of the medical imaging device and the medical images, etc. In some embodiments, the second medical data may include a test sample set. The test sample set may include a set of scan data samples, a set of medical image samples, etc. The processing device 120 may obtain the second medical data in a similar manner as obtaining the first medical data. For example, the processing device 120 may obtain the second medical data directly from a storage device (the storage device 130) or a user input. As another example, the processing device 120 may obtain the scan data directly from the medical imaging device as the second medical data.

In some embodiments, the processing device 120 may divide the medical data stored in the storage device into the first medical data and the second medical data in accordance with a preset rule. The preset rule may be in a particular ratio. For example, the processing device 120 may divide the stored medical data according to a ratio of 7:3, the divided medical data with a greater percentage is the first medical data, and the divided medical data with a smaller percentage is the second medical data.

The test result refers to a processing result of the medical data processing network, i.e., the output of the medical data processing network. For example, the test result may include a processed medical image such as noise reduced medical image, artifact removed medical image, etc. In some embodiments, after obtaining the second medical data, the processing device 120 may input the second medical data into the second network to obtain the test result. The test result may be the output of the second network.

In step 240, an evaluation result of a performance of the second network is determined based on the test result. In some embodiments, step 240 may be performed by an evaluation unit 954 illustrated in FIG. 9.

In some embodiments, after obtaining the test result of the second network, the processing device 120 may evaluate the performance of the second network based on the test result, and determine an evaluation result of the performance of the second network. The evaluation may be performed automatically or manually. The evaluation result may be used to characterize whether the performance of the medical data processing network satisfies a user requirement. The user requirement is preset by the user. According to the user requirement, whether the performance of the medical data processing network satisfies the user requirement may include at least one of whether a processing efficiency (a processing speed) (e.g., a speed of the second network outputting the result) of the network satisfies the user requirement, whether the processing quality (the quality of the output medical image) of the network satisfies the user requirement, etc.

In some embodiments, the processing device 120 or the terminal 140 may display the test result on an application interface. The present disclosure does not limit the specific ways of displaying, e.g., the processing device 120 or the terminal 140 may display the medical images directly, etc. The user (e.g., a physician, a model tester, etc.) may evaluate the test result based on the user requirement. For example, the user may assess whether the noise, the artifacts, etc., of the images output by the second network reach a standard, and if they reach the standard, it may be determined that the evaluation result is that the performance of the second network satisfies the requirement; if they are does not reach the standard, it may be determined that the assessment result is that the performance of the second network does not satisfy the requirement. By displaying the test result on the application interface, the user may intuitively understand the test result, so as to determine whether the trained medical data processing network (i.e., the second network) satisfies the requirement by combining with user own demand, thus satisfying personalized and diversified demands of the user.

In some embodiments, the user may indicate the determination of the evaluation result by triggering a specific instruction on the application interface. Specifically, the user may indicate, by triggering a confirmation instruction on the application interface, that the evaluation result is the performance of the second network satisfies the requirement; the user may indicate, by triggering a retraining instruction on the application interface, that the evaluation result is the performance of the second network does not satisfy the requirement, thus the network needs to be retrained. In some embodiments, the triggering of the instruction may be performed via a trigger control component.

In some embodiments, the processing device 120 may automatically determine the evaluation result based on the test result. For example, the processing device 120 may automatically evaluate the test result, such as through the machine learning model. The input of the machine learning model may be an input image and an output image of the second model, and the output of the machine learning model may be the evaluation result. The machine learning model may be obtained by training using a great amount of historical evaluation data of the user. The training samples may be image samples before and after processing from the historical evaluation data, and the labels are evaluation results corresponding to the image samples.

In some embodiments, in response to receiving the confirmation instruction, the processing device 120 may determine that the evaluation result indicates that the performance of the second network satisfies the requirement. For example, both the processing efficiency and the processing quality of the second network satisfy the user requirement. In response to receiving the retraining instruction, the processing device 120 may determine that the evaluation result indicates that the performance of the second network does not satisfy the requirement. For example, at least one of the processing efficiency and the processing quality of the second network does not satisfy the user requirement. It is simple, intuitive and operable to determine the evaluation result through different instructions triggered by the user on the application interface to determine whether the performance of the trained medical data processing network (the second network) satisfies the requirement.

In Step 250, in response to the evaluation result indicating that the performance of the second network satisfies a requirement, a parameter of the second network is stored. In some embodiments, step 250 may be performed by a determination unit 955 illustrated in FIG. 9.

In some embodiments, in response to the evaluation result indicating that the performance of the second network satisfies the requirement, the processing device 120 may store the parameter of the second network. The storage may be performed in various manners, which are not limited in the present disclosure. For example, the processing device 120 may store the parameter of the second network on a local or a remote storage device. As another example, the processing device 120 may store the parameter of the second network in a centralized or distributed manner.

In some embodiments, the processing device 120 may label the parameter of the second network to obtain a labeled parameter. The label may be related to at least one of a function, a type of the second network. The label may be a letter or a count, etc. In some embodiments, the processing device 120 may add a recognizable field to the parameter of the second network to obtain the labeled parameter. In some embodiments, the processing device 120 may obtain the labeled parameter by establishing an associative relationship between the parameter of the second network and the label corresponding to the parameter. Merely by way of example, assuming that the parameter of the second network is denoted as B, and a function of the second network is segmenting the medical image, which is denoted as 1, and that the type of the second network is a CNN network, which is denoted as II, then the labeled parameter may be denoted as B1II or B-1-II.

The processing device 120 may store the labeled parameter. By labeling and storing the parameter of the trained medical data processing network (i.e., the second network) according to the function and/or type of the network, the stored network parameter may be well-organized, and the user may later access the parameter in a targeted manner according to the labeled parameters, which facilitates a rapid access to the network parameter, and improves the processing efficiency. For example, if the user needs a noise reduction network, the user may directly obtain the parameter of the noise reduction type network based on the labeling of the parameter, and generate the noise reduction network based on the obtained parameter without going through a step of determining the type of network corresponding to the parameter.

In some embodiments, in response to that the evaluation result indicates that the performance of the second network does not satisfy the requirement, the processing device 120 may retrain the network (e.g., the first network, the second network) based on the new first medical data until a medical data processing network with a performance that satisfies the requirement is obtained. For specifics on how to retrain the network, please refer to FIG. 6.

According to embodiments of the present disclosure, the training of the medical data processing network may be performed directly on the medical imaging system instead of going through an external supplier. In this way, a data source of the network to be trained is not limited, and new medical data (e.g., new clinical scenarios) may be used timely, which improves the generalization ability of the network and enables the network to adapt to the new clinical scenarios timely. Further, according to the embodiments of the present disclosure, the network may be tested based on the second medical data and the performance of the network may be evaluated by the test result, which makes the parameter of the generated network more accurate and the generated network more reliable and practical. In addition, the network is trained using an unsupervised training, which eliminates a need to obtain a great count of training samples (e.g., the first medical data) and does not require labeling of the training samples, resulting in a low hardware requirement, and greatly saving a training cost.

Figure 4:
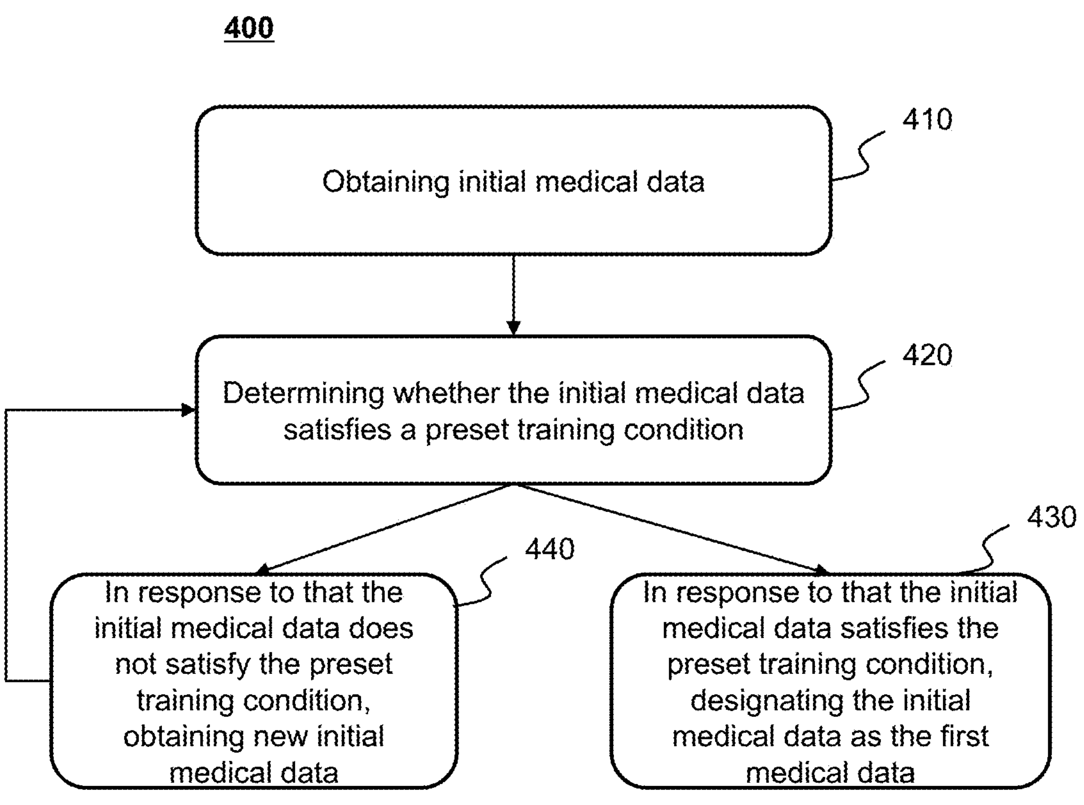
FIG. 4 is a flowchart illustrating an exemplary process for determining first medical data according to some embodiments of the present disclosure.

FIG. 4 is a flowchart illustrating an exemplary process for determining first medical data according to some embodiments of the present disclosure. In some embodiments, at least a portion of the process 400 may be performed to achieve at least a portion of step 210 as described in FIG. 2. For example, the processing device 120 may obtain the first medical data by performing at least a portion of the process 400.

In step 410, initial medical data is obtained.

The initial medical data refers to raw, unprocessed scan data of a medical imaging device (e.g., the imaging device 110). For example, the initial medical data may include computerized tomography (CT) scan data, magnetic resonance (MR) scan data, positron emission computed tomography (PET) scan data, etc. The processing device 120 may obtain the initial medical data using any feasible means, which is not limited by the present disclosure. For example, the processing device 120 may obtain the initial medical data by instructing the medical imaging device to scan a target object (e.g., a human body, a mold, etc.). As another example, the processing device 120 may obtain the initial medical data from a storage device (e.g., the storage device 130). As yet another example, the processing device 120 may obtain the initial medical data from a picture archiving and communication system (PACS) server at a hospital.

In step 420, whether the initial medical data satisfies a preset training condition is determined.

The preset training condition may include at least one of whether a volume of the initial medical data reaches a preset volume threshold, and whether the initial medical data is accurate, or whether a size of the initial medical data satisfies a preset size threshold. The volume of the initial medical data refers to a volume of a data group of the initial medical data. For example, the data obtained for each scan or corresponding to each patient may be a data group.

The preset volume threshold may be related to at least one of a function of a first network or a training progress of the first network, etc. For example, the preset volume thresholds corresponding to the networks for an image reconstruction, a post-processing, and an image segmentation may be different. As another example, the preset volume threshold corresponding to the first network at an early stage of training may be higher than the preset volume threshold corresponding to the first network at a later stage of training. By determining the training data of the first network based on the function and the training progress of the first network, the training data may adapt to the networks with different functions and training states, and the generalization ability of the generated network may be improved.

In some embodiments, the preset volume threshold may be determined in other ways. For example, the preset volume threshold may be determined via a vector database, which includes a reference vector (network function of the first network) and a reference preset quantity threshold corresponding to the reference vector. The specific determination method is similar to the method of determining the preset training frequency via the vector database in step 220. As another example, the preset count threshold may be determined by a machine learning model, and the specific determination method is similar to the method of determining the preset training frequency by the machine learning model in step 220.

The whether the initial medical data is accurate refers to whether the data obtained by the processing device 120 is consistent with the raw scan data. For example, the raw scan data may be damaged during transmission, causing the data (i.e., the initial medical data) received by the processing device 120 to be different from the raw scan data. The processing device 120 may determine whether the initial medical data is accurate by data calibration (e.g., by Cyclic Redundancy Check (CRC), MD5, etc.). The size of the initial medical data refers to a size of each group of data of the initial medical data. For example, the size of the scan data for each PET scan may be 1 G or 2G, etc. In general, the greater the data, the more noise. The preset size threshold may be determined based on a scan type (e.g., CT, MR, PET, etc.) or a scan site/position, etc. For example, the preset size thresholds corresponding to the CT scan and the PET scan may be different. As another example, the preset size threshold corresponding to a chest scan and the preset size threshold corresponding to a brain scan may be different. In some embodiments, the preset size threshold may be determined in other ways. For example, the preset size threshold may be determined via a vector database, which includes a reference vector (the network function of the first network) and a reference preset size threshold corresponding to the reference vector. The specific determination method is similar to the method of determining the preset training frequency via the vector database in step 220. As another example, the preset size threshold may be determined by the machine learning model, and the specific determination method is similar to the method of determining the preset training frequency by the machine learning model in step 220.

In step 430, in response to that the initial medical data satisfies the preset training condition, the initial medical data is designated as the first medical data.

In step 440, in response to that the initial medical data does not satisfy the preset training condition, new initial medical data is obtained.

In some embodiments, in response to that the initial medical data does not satisfy the preset training condition, the processing device 120 may obtain the new initial medical data, which is obtained in the same or similar manner as the initial medical data in step 410. After obtaining the new initial medical data, the processing device 120 returns to perform step 420 to determine whether the new initial medical data satisfies the preset training condition. If the new initial medical data satisfies the preset training condition, the processing device 120 performs step 430 to designate the new initial medical data as the first medical data. If the new initial medical data does not satisfy the preset training condition, the processing device 120 reperforms steps 440 and 420 again until the initial medical data satisfying the preset training condition is obtained.

According to the embodiments provided in the present disclosure, by obtaining the initial medical data and determining the training sample (the first medical data) for training the medical data processing network (the first network) based on whether the initial medical data satisfies the preset training condition, the accuracy of the training sample used in training the medical data processing network (the first network) is improved, so that the obtained target medical data processing network (the second network) is more accurate, thereby improving a reliability and a usefulness of the process of determining the medical data processing network.

Figure 5:
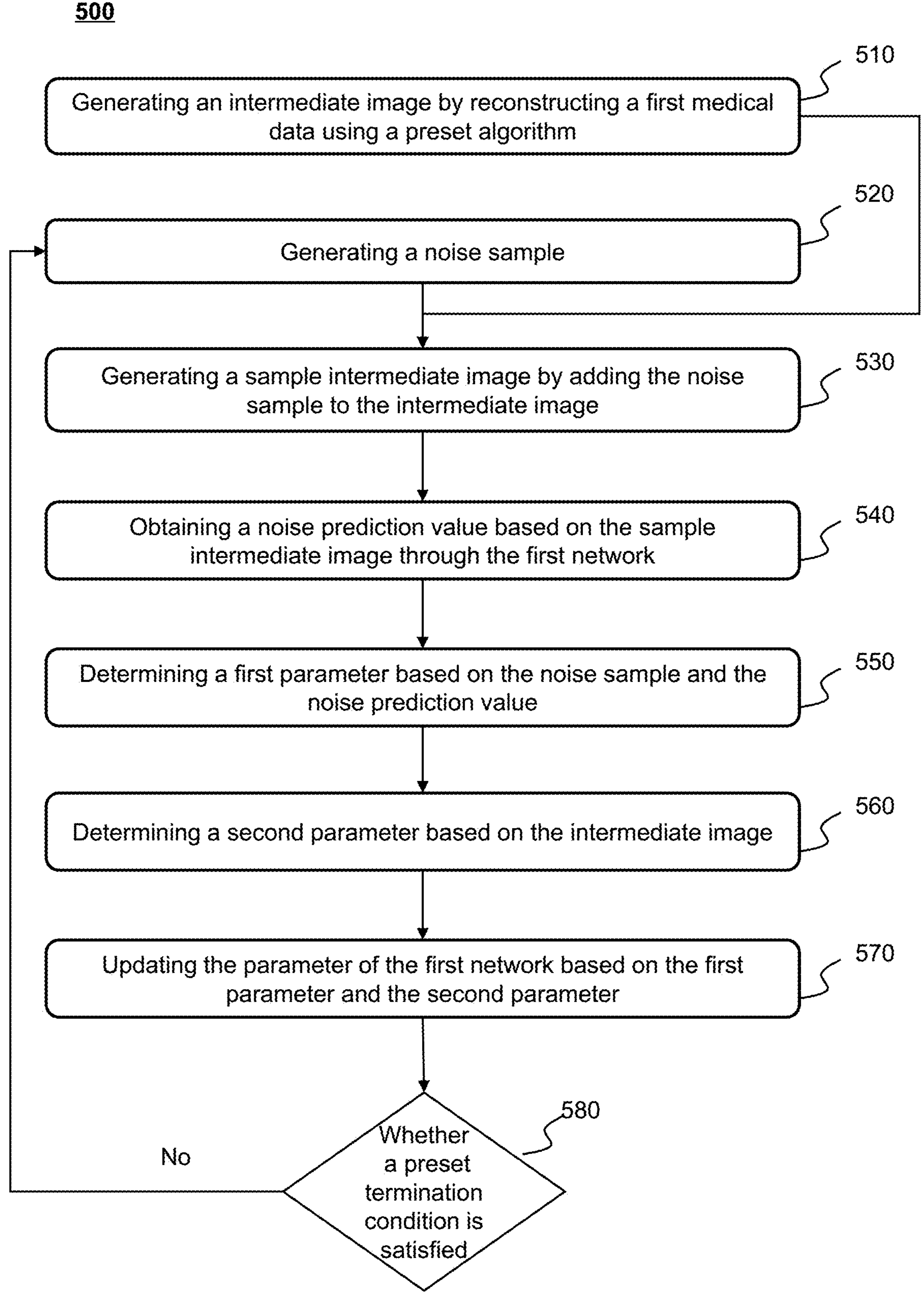
FIG. 5 is a flowchart illustrating an exemplary process for training a first network according to some embodiments of the present disclosure.

FIG. 5 is a flowchart illustrating an exemplary process for training a first network according to some embodiments of the present disclosure. In some embodiments, at least a portion of a process 500 may be performed to achieve at least a portion of the step 220 as described in FIG. 2. For example, the processing device 120 may train the first network by performing at least a portion of the process 500 to obtain a second network. Merely by way of example, the process 500 is illustrated with the first network, the second network, and the third network all being noise reduction networks.

Step 510, an intermediate image is generated by reconstructing a first medical data using a preset algorithm.

In some embodiments, after step 210, the processing device 120 may reconstruct the first medical data using the preset algorithm to generate the intermediate image. The preset algorithm may include various reconstruction algorithms, for example, a parsing algorithm, an iterative algorithm, etc. The iterative algorithm may include various algorithms such as an expectation maximization (EM), a maximum likelihood expectation maximization (MLEM) algorithm, an ordered subset expectation maximization (OSEM) algorithm, etc.

In some embodiments, the processing device 120 may train the first network based on the intermediate image by adding image quality interference information to the intermediate image. The image quality interference information may include at least one of noise, an artifact, etc. For example, if the first network, the second network, and the third network are artifact removal networks, the processing device 120 may add artifacts to the intermediate image. For another example, if the first network, the second network, and the third network are noise reduction networks, the processing device 120 may add noise to the intermediate image. In some embodiments, the processing device 120 may perform adding the noise to the intermediate image by iteratively performing the operations shown in steps 520-step 580. Through training the first network based on the reconstructed image by performing an image reconstruction on the first medical data, the first network only needs to focus on processing the image, which makes the first network more targeted, and reduces a network size the first network, making it simpler.

In some embodiments, the processing device 120 may perform a noise reduction on the intermediate image to obtain a noise reduced image to train the first network based on the noise reduced image. The noise reduction may be performed using any feasible noise reduction manners, and the present specification does not limit this. For example, the processing device 120 may use a noise reduction algorithm for noise reduction, or may perform the noise reduction via a machine learning models, etc. By performing the noise reduction on the reconstructed image, the quality of the image sample used for model training is improved, resulting in a better performance of the trained first network.

In step 520, a noise sample is generated.

In some embodiments, the processing device 120 may generate the noise sample in various ways. For example, the processing device 120 may select a noise distribution from a noise distribution set as the noise sample. The noise distribution may be a Gaussian distribution or a Poisson distribution, in other words, a distribution of the noise sample conforms to the Gaussian distribution or the Poisson distribution. The noise sample may be selected randomly or in a preset sequence. The processing device 120 may determine a generation parameter of the noise distribution set based on a function and a network complexity of the first network. The generation parameter at least includes a size of the noise distribution set, i.e., a count of noise distributions in the noise distribution set. For example, the generation parameters (e.g., a size of the noise distribution set) corresponding to the image reconstruction network, a post-processing network, and an image segmentation network may be different. As another example, the higher the network complexity, the greater the noise distribution set. Further, the processing device 120 may obtain, based on the generation parameter, a certain count of noise distributions to form the noise distribution set. By selecting the noise distributions from the noise distribution set as the noise sample, a randomness of the noise sample may be improved, which makes the subsequent image samples generated by adding the noise sample broadly representative, so as to improve a generalization ability of the generated medical data processing network (the second network).

The generation parameter may also include a mean step as well as a standard deviation step. The mean step refers to a difference between means of two neighboring noise distributions in a mean sequence. The processing device 120 may perform a mean sort on the distributions in the generated noise distribution set according to the mean step. The standard deviation step refers to a difference between standard deviations of two neighboring noise distributions in a standard deviation sequence. The processing device 120 may perform a standard deviation sort on the distributions in the generated noise distribution set according to the standard deviation step.

In some embodiments, the processing device 120 may determine the generation parameter via a vector database. The vector database for determining the generation parameters includes a reference vector (e.g., a vector of at least one of the function and the network complexity of the first network) and a reference generation parameter corresponding to the reference vector. The specific determination method is similar to the method of determining the preset training frequency via the vector database in step 220.

In some embodiments, the processing device 120 may determine the generation parameter via the machine learning model. A type of the machine learning model may include a CNN, RNN, or LSTM, etc. An input of the model is at least one of a function and a network complexity of the first network, etc., and an output of the model is the generation parameter. The specific determination method is similar to the method of determining the preset training frequency by the machine learning model in step 220.

In some embodiments, the processing device 120 may determine the generation parameter via the machine learning model based on the function of the first network, the complexity of the network, and a distribution of prior information. The processing device 120 may extract average image features (e.g., an image resolution, a noise level, etc.) from a great count of pre-obtained medical images, and take the average image features as the distribution of the priori information. An input of the model is the functions of the first network, the network complexity of the first network, and the distribution of the priori information, and an output of the model is the generation parameter.

In step 530, a sample intermediate image is generated by adding the noise sample to the intermediate image.

The operation of adding the noise sample may be performed iteratively for a count of times, i.e., the processing device 120 may add the noise sample to the intermediate image for a count of times until an iteration stop condition is satisfied. For example, the iteration stop condition may be that a count of iterations reaches a preset value or that the noise level of the sample intermediate image reaches a preset standard, etc.

In some embodiments, in a training process, the count of times the processing device 120 adds the noise sample to the intermediate image may be correlated with the network complexity of the first network. For example, the higher the network complexity, the higher the count of times the noise sample is added. Usually, the higher the network complexity, the better a noise reduction ability of the network. By increasing the count of times that the noise sample is added during the training process, the network with better noise reduction ability may be obtained.

In some embodiments, the count of times the processing device 120 adds the noise sample to the intermediate image may be determined in other ways. For example, the count of times for adding the noise sample may be determined by the vector database. The vector database includes the reference vector (e.g., a vector of the network complexity of the first network) and a reference count of times for adding the noise sample that corresponds to the reference vector. As another example, the count of times for adding the noise sample may be determined via a machine learning model. An input of the model is the network complexity of the first network and an output of the model is the count of times for adding the noise sample.

In step 540, a noise prediction value is obtained based on the sample intermediate image through the first network.

Specifically, the processing device 120 may input the sample intermediate image into the first network to obtain an output image. The processing device 120 may perform, by the first network, a noise reduction processing on the sample intermediate image. The processing device 120 may use the sample intermediate image after the noise reduction as the output image. The processing device 120 may obtain a noise prediction value based on a difference between the input sample intermediate image and the output image.

In step 550, a first parameter is determined based on the noise sample and the noise prediction value.

In some embodiments, the processing device 120 may construct a loss function based on the noise sample and the noise prediction value, and obtain the first parameter based on the loss function. The first parameter is also referred to as a regularization term.

In step 560, a second parameter is determined based on the intermediate image.

In some embodiments, the processing device 120 may determine the second parameter based on the intermediate image using an expectation maximum (EM) algorithm. The second parameter is also referred to as a data fidelity term.

In step 570, the parameter of the first network is updated based on the first parameter and the second parameter.

In some embodiments, the processing device 120 may update the parameter of the first network based on the first parameter and the second parameter. The processing device 120 may maximize a sum of the first parameter and the second parameter by updating the parameter of the first network.

In step 580, whether a preset termination condition is satisfied is determined.

In some embodiments, after updating the parameter of the first network, the processing device 120 may determine whether the preset termination condition is satisfied. The preset termination condition may include a count of iterations reaching a preset count of times, the parameter of the first network no longer varying, the output image of the first network satisfying a quality requirement, etc. In response to that the preset termination condition is satisfied, the processing device 120 may determine the first network at this time to be the second network. In response to that the preset termination condition is not satisfied, the processing device 120 may continue to iteratively perform the operations of steps 520-580 until the preset termination condition is satisfied.

According to the embodiments of present disclosure, by iteratively updating the parameter of the first network, the obtained second network has a stronger generalization ability, thereby improving the noise reduction ability of the second network, and accordingly improving the noise reduction effect of the output image.

Figure 6:
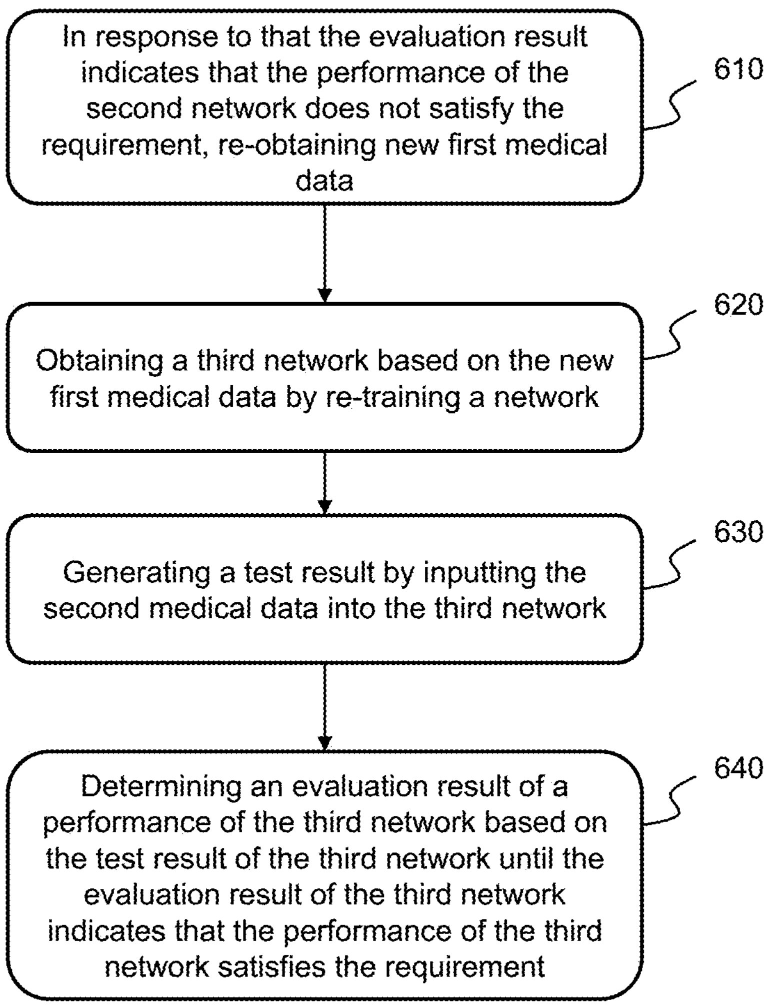
FIG. 6 is a flowchart illustrating an exemplary process for medical data processing according to some embodiments of the present disclosure.

FIG. 6 is a flowchart illustrating an exemplary process for medical data processing according to some embodiments of the present disclosure. In some embodiments, at least a portion of a process 600 may be performed to achieve at least a portion of the step 240 in FIG. 2. For example, when an evaluation result indicates that a performance of a second network does not satisfy a requirement, the processing device 120 may obtain a third network whose performance satisfies the requirement by performing at least a portion of the steps of the process 600.

In step 610, in response to that the evaluation result indicates that the performance of the second network does not satisfy the requirement, new first medical data is re-obtained.

In some embodiments, after step 240 in FIG. 2, in response to an evaluation indicating that the performance of the second network does not satisfy the requirements, the processing device 120 may re-obtain the new first medical data. The manner of obtaining the new first medical data may be the same or similar to the manner of obtaining the first medical data in step 210.

In step 620, a third network is obtained based on the new first medical data by re-training a network.

In some embodiments, the network may be the second network, and the processing device 120 may train the second network to obtain the third network based on the new first medical data in the same manner as the manner of training the first network. Specifically, the processing device 120 may use the new first medical data to train the second network to obtain the third network by performing operations similar to those in steps 220-250 in FIG. 2.

In some embodiments, the network may be the first network, and the processing device 120 may re-train the first network to obtain the third network based on the new first medical data. Specifically, the processing device 120 may use the new first medical data to re-train the first network to obtain the third network by performing the operations in steps 220-250 in FIG. 2.

In step 630, a test result is generated by inputting the second medical data into the third network. For contents on how to generate the test result, please refer to step 230 in FIG. 2.

In step 640, an evaluation result of a performance of the third network is determined based on the test result of the third network until the evaluation result of the third network indicates that the performance of the third network satisfies the requirement.

The processing device 120 may determine the evaluation result of the performance of the third network based on the test results of the third network in a manner similar to step 240 in FIG. 2. in response to that the evaluation result indicates that the performance of the third network satisfies the requirement, the processing device 120 may store the parameter of the third network in a manner similar to step 250 in FIG. 2. In response to that the evaluation result indicates that the performance of the third network does not satisfy the requirement, the processing device 120 may re-train the network by repeating the steps in the process 600 until the evaluation result of the third network indicates that the performance of the third network satisfies the requirement.

According to the embodiments of the present disclosure, by obtaining the new first medical data and re-training the medical data processing network whose performance does not satisfy the requirement based on the new medical data, the finally obtained medical data processing network may well satisfy the requirement of the user.

Figure 7:
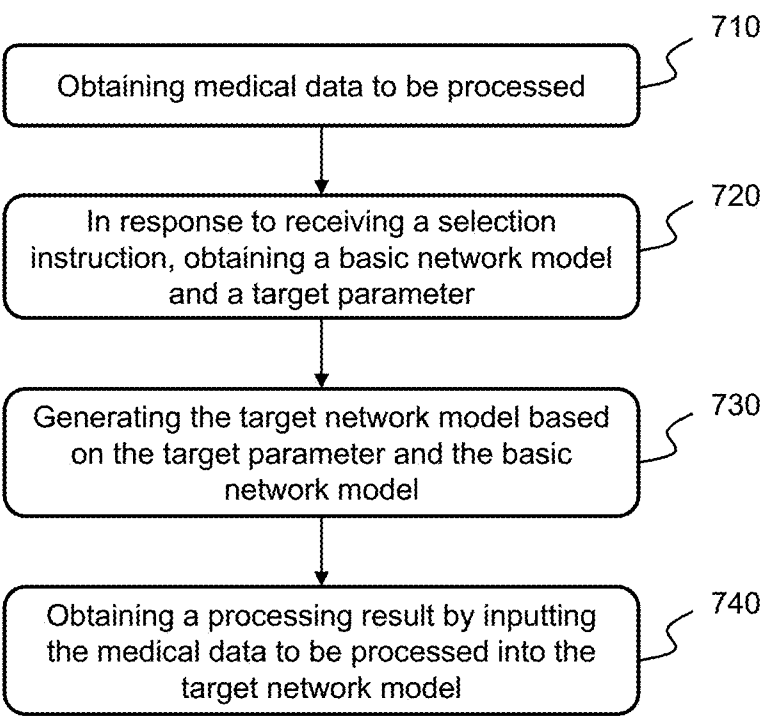
FIG. 7 is a flowchart illustrating an exemplary process for medical data processing according to some embodiments of the present disclosure.

FIG. 7 is a flowchart illustrating an exemplary process for medical data processing according to some embodiments of the present disclosure. In some embodiments, a process 700 may be performed by the medical imaging system 100 (e.g., the processing device 120). For example, the process 700 may be implemented as a group of instructions (e.g., an application) stored in a storage device (e.g., the storage device 130 in FIG. 1). In some embodiments, the processing device 120 of the medical imaging system 100 and/or one or more modules of the processing device 120 in FIG. 9 may perform the group of instructions and may accordingly be directed to perform the process 700.

In step 710, medical data to be processed is obtained.

In some embodiments, the processing device 120 may obtain the medical data to be processed. The medical data to be processed may include raw scan data, an image, etc. There may be various kinds of the medical data to be processed. For example, when the medical data to be processed is the raw scan data, the medical data processing may include an image reconstruction of the raw scan data, etc. As another example, when the medical data to be processed is the image, the medical data processing may include performing at least one of a noise reduction, an artifact removal, an image registration, an image segmentation, etc. on the image. The processing device 120 may obtain the medical data to be processed in various feasible ways, which are not limited in the present disclosure. For example, the processing device 120 may obtain the medical data to be processed in a manner similar to the manner the processing device 120 obtains the first medical data and the second medical data in process 200, and the manner the processing device 120 obtains the initial medical data in process 400.

Merely by way of example, a user may perform a triggering operation on a control component of a medical data processing network on an application interface. In response to the triggering operation, a use instruction may be generated, and the processing device 120 may present a reminding message to the user based on the use instruction to remind the user to enter the medical data to be processed. After receiving the medical data to be processed entered by the user, the processing device 120 may process the medical data to be processed using the medical data processing network. The medical data processing network is a medical data processing network provided by a supplier, or a target network determined through steps 720-730.

In step 720, in response to receiving a selection instruction, a basic network model and a target parameter are obtained.

The basic network model is a basic model used to generate the medical data processing network. The basic network model is a network whose performance does not satisfy the requirement of the user. The basic network model may include untrained or trained networks. For example, the basic network model may be the first network. The target parameter refers to a network parameter for generating the medical data processing network, which is a user-selected network parameter. In some embodiments, in response to receiving the selection instruction, the processing device 120 may obtain the basic network model and the target parameter. The selection instruction is triggered by the user on the application interface of a computing device, and the selection instruction is configured to select the target parameter from a plurality of parameters and select the basic network model from a plurality of network models. In some embodiments, the medical imaging system (e.g., the medical imaging system 100) may include a self-training network application mode, by which the user selects the basic network model and the target parameter.

Merely by way of example, the user may generate a selection instruction on the application interface by triggering an operation on the network selection control component, and the selection instruction may include the target parameter selected by the user from the plurality of parameters, and the basic network model selected by the user from the plurality of network models. The processing device 120, upon receiving the selection instruction, may obtain the basic network model and the target parameter therefrom.

Merely by way of example, the user may perform the triggering operation on the self-training network on the application interface using the control component, and a terminal displays a network parameter display interface in response to the triggering operation. There are a plurality of network parameters displayed on the network parameter display interface. The user may perform the triggering operation with respect to the target parameter on the network parameter display interface, and the terminal generates the selection instruction in response to the triggering operation, and the processing device 120 may obtain the target parameter based on the selection instruction.

In some embodiments, the plurality of parameters for selecting the target parameter may be obtained in the following manner: in response to receiving the training instruction, the processing device 120 may obtain the first medical data. The training instruction is triggered by the user on the application interface. The processing device 120 may train the first network based on the first medical data to obtain a second network. The training includes an unsupervised training. The processing device 120 may input the second medical data into the second network to generate a test result. The second medical data includes a test sample set. The processing device 120 may determine an evaluation result of the performance of the second network based on the test result, and further, in response to the evaluation result indicating that the performance of the second network satisfies the requirement, the processing device 120 may designate a parameter of the second network as one of the plurality of parameters. For more contents on how to obtain the plurality of parameters, please refer to FIG. 2, FIG. 4, FIG. 5, and FIG. 6. In some embodiments, the medical imaging system (e.g., the medical imaging system 100) may include the self-training network mode by which the user trains the selected first network to obtain the second network and the parameters thereof. In some embodiments, the self-training network mode may also be included in the self-training network application mode. The user may choose to select only the basic network model, and the processing device 120 may automatically take the basic network model as the first model for training, and use the second model obtained from the training as the target network model.

In step 730, the target network model is generated based on the target parameter and the basic network model.

The target network model is a medical data processing network whose performance satisfies the requirement of the user. For example, the target network model may be the second network or the third network. In some embodiments, the processing device 120 may generate the target network model based on the target parameter and the basic network model. Specifically, the processing device 120 may replace the parameter of the base network model with the target parameter to obtain the target network model.

In step 740, a processing result is obtained by inputting the medical data to be processed into the target network model.

In some embodiments, the processing device 120 may input the medical data to be processed into the target network model to obtain the processing result. Specifically, the processing device 120 may input the medical data to be processed into the target network model, and take the output of the target network model as the processing result. A type of the processing result is determined by a type of the target network model. For example, if the target network model is an image reconstruction model, the processing result is a reconstructed image obtained by reconstructing the medical data to be processed. For another example, if the target network model is the noise reduction model, the processing result is the medical image obtained from the medical data to be processed by noise reduction.

According to the embodiments of the present disclosure, the target network model is obtained by self-selecting the basic network model and the target parameter required for generating the model. The target parameter is obtained by the unsupervised training of the medical data processing network. In this way, the user may select the desired medical data processing network according to the requirement, and the network may be generated in real time, which facilitates a use of the user and improves an efficiency of the use. Moreover, as the network is trained based on data provided by the user, the generalization ability of the network is improved.

Figure 8:
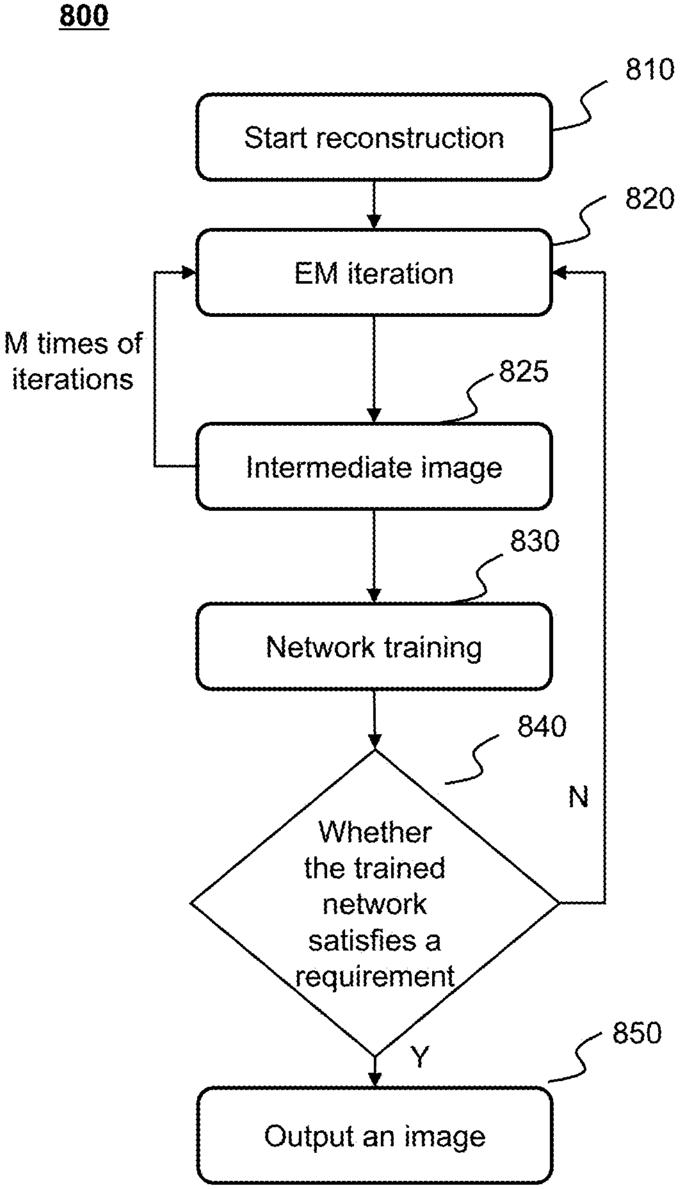
FIG. 8 is a flowchart illustrating an exemplary process for performing an offline reconstruction on a medical image according to some embodiments of the present disclosure.

FIG. 8 is a flowchart illustrating an exemplary process for performing an offline reconstruction of a medical image according to some embodiments of the present disclosure. In some embodiments, at least a portion of a process 800 may be performed to achieve at least a portion of steps as described in connection with FIG. 2.

As shown in FIG. 8, the processing device 120 may collect scan data via a medical imaging device (e.g., the imaging device 110). In step 810, the processing device 120 starts a reconstruction based on the scan data. The reconstruction may be performed during spare time when the medical imaging device is not scanning a patient. Merely by way of example, the processing device 120 may start an automated reconstruction script that performs a training data condition check on the scan data, and after determining that the training data condition is satisfied, an offline reconstruction may be started. The reconstruction process may include the operations of steps 820-850.

In step 820, the processing device 120 performs EM iterations. Specifically, the processing device 120 may perform an image reconstruction on the scan data using an EM algorithm (e.g., a maximum likelihood expectation maximization (MLEM) algorithm, an ordered subset expectation maximization (OSEM) algorithm, etc.) to obtain an intermediate image 825. The image reconstruction may be performed iteratively for M times. For more contents on how to obtain the intermediate image, please refer to step 510.

In step 830, the processing device 120 may perform the network training based on the intermediate image 825. The network used for training may be an untrained or a trained medical data processing network. For example, the network used for training may be a first network, a basic network model, etc. The network training includes the unsupervised training. The training process may be represented as: $x'=\arg\max(L_{(x)}+R_{(x)})$, where x' denotes an output image of the network, $R_{(x)}$ denotes a first parameter of the network, $L_{(x)}$ denotes a second parameter of the network, and $\max(L_{(x)}+R_{(x)})$ denotes maximizing a sum of $L_{(x)}$ and $R_{(x)}$. For more contents on network training, please refer to steps 520-570.

In step 840, the processing device 120 may determine whether the trained network satisfies a requirement. In response to that the network satisfies the requirement, the processing device may perform step 850. In response to that the network does not satisfy the requirement, the processing device may return to perform step 820. For specifics on how to determine whether a trained network satisfies the requirement, please refer to step 580.

In step 850, the processing device 120 may input the intermediate image 825 into the trained network and output an image. The output image is the image processed by the network. For example, the output image may be an image undergoes at least one of a noise reduction, an artifact removal, an image registration, an image segmentation, etc.

Figure 9:
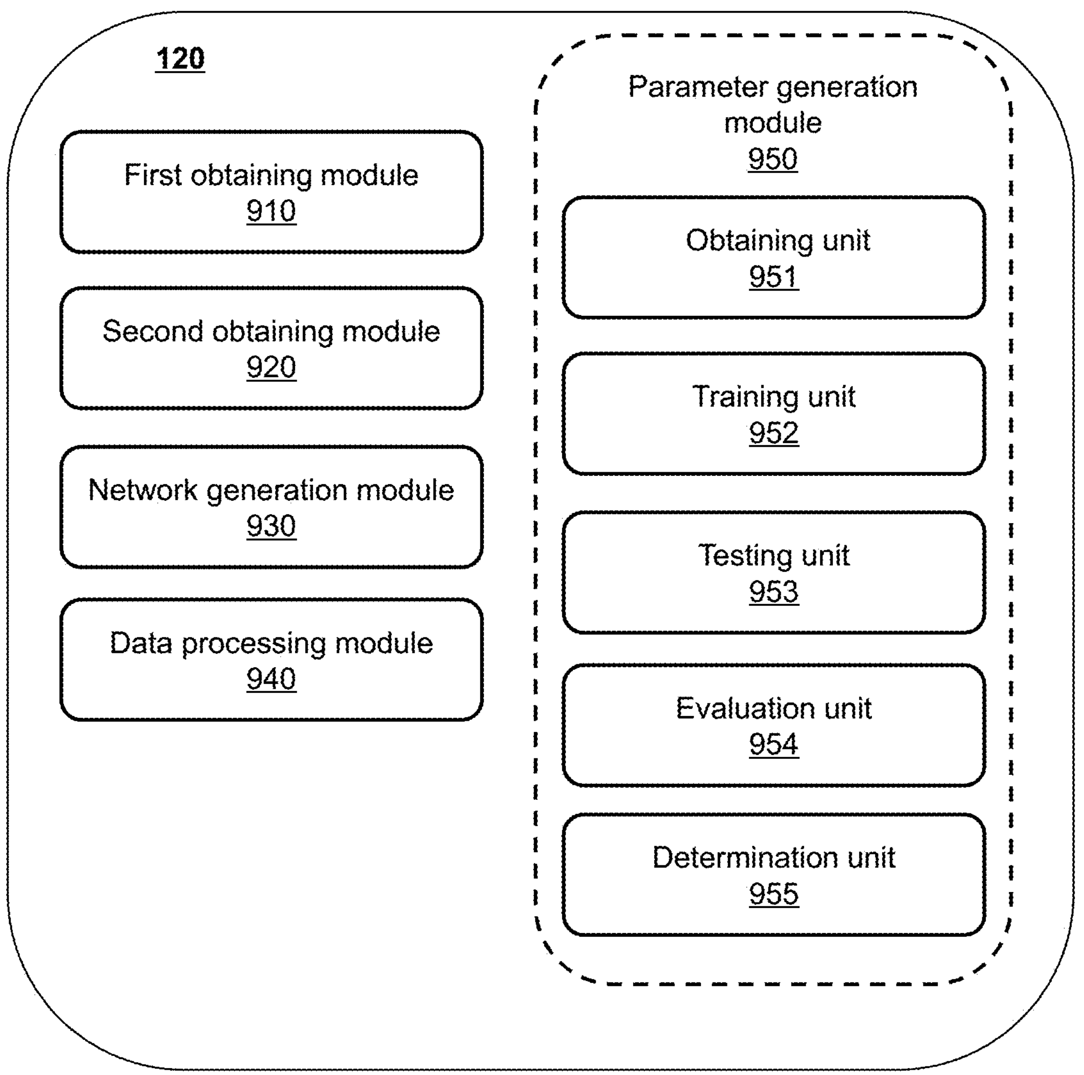
FIG. 9 is a block diagram illustrating an exemplary processing device according to some embodiments of the present disclosure.

FIG. 9 is a block diagram illustrating an exemplary processing device according to some embodiments of the present disclosure. As shown in FIG. 9, the processing device 120 includes a first obtaining module 910, a second obtaining module 920, a network generation module 930, and a data processing module 940.

The first obtaining module 910 may be configured to obtain medical data to be processed. For more contents on obtaining the medical data to be processed, please refer to elsewhere in the present disclosure (e.g., step 710 and the descriptions thereof).

The second obtaining module 920 may be configured to obtain a basic network model and a target parameter in response to receiving a selection instruction. The selection instruction is triggered by a user on an application interface of the processing device 120. The selection instruction is configured to select the target parameter from a plurality of parameters and select the basic network model from a plurality of network models. For more contents on the obtaining the basic network model and the target parameter, please refer to elsewhere in the present disclosure (e.g., step 720 and the descriptions thereof).

In some embodiments, the processing device 120 may further include a parameter generation module 950. The parameter generation module 950 may be configured to generate the plurality of parameters. The parameter generation module 950 may include an obtaining unit 951, a training unit 952, a testing unit 953, an evaluation unit 954, and a determination unit.

The obtaining unit 951 may be configured to obtain a first medical data in response to receiving a training instruction. The training instruction is triggered by a user on an application interface. For more descriptions on obtaining the first medical data, please refer to elsewhere in the present disclosure (e.g., step 210 and the descriptions thereof).

The training unit 952 may be configured to train a first network based on the first medical data to obtain a second network. The training includes an unsupervised training. For more descriptions of the obtaining the second network, please refer to elsewhere in the present disclosure (e.g., step 220 and the descriptions thereof).

The testing unit 953 may be configured to generating a test result by inputting second medical data into the second network. The second medical data includes a test sample set. For more descriptions of the generation of the test result, please refer to elsewhere in the present disclosure (e.g., step 230 and the descriptions thereof).

The evaluation unit 954 may be configured to determine an evaluation result of a performance of the second network based on the test result. For more descriptions of the determination of the evaluation result, please refer to elsewhere in the present disclosure (e.g., step 240 and the descriptions thereof).

The determination unit 955 may be configured to designate a parameter of the second network as one of the plurality of parameter in response to the evaluation result indicating that the performance of the second network satisfies a requirement. The determination unit 955 may also be configured to store the parameter of the second network in response to the evaluation result indicating that the performance of the second network satisfies the requirement. For more contents of the determining the plurality of parameters and the storing the parameter of the second network, please refer to elsewhere in the present disclosure (e.g., step 720, step 250 and the descriptions thereof).

The network generation module 930 may be configured to generate a target network model based on the target parameter and the basic network model. For more contents of the generating the target network model, please refer to elsewhere in the present disclosure (e.g., step 730 and the descriptions thereof).

The data processing module 940 may be configured to obtain a processing result by inputting the medical data to be processed into the target network model. For more contents on the obtaining the processing result, please refer to elsewhere in the present disclosure (e.g., step 740 and the descriptions thereof).

It should be noted that the above descriptions of the processing device 120 are provided for the purposes of illustration, and are not intended to limit the scope of the present disclosure. For those skilled in the art, various modifications and changes in the forms and details of the application of the above system may occur without departing from the principles of the present disclosure. In some embodiments, the processing device 120 may include one or more other modules and/or one or more modules described above may be omitted. Additionally or alternatively, two or more modules may be integrated into a single module and/or a module may be divided into two or more units. However, those variations and modifications also fall within the scope of the present disclosure.

The operations of the illustrated processes 200, 400, 500, 600, 700, and 800 presented above are intended to be illustrative. In some embodiments, a process may be accomplished with one or more additional operations not described, and/or without one or more of the operations discussed. Additionally, the order in which the operations of a process described above is not intended to be limiting.

Having thus described the basic concepts, it may be rather apparent to those skilled in the art after reading this detailed disclosure that the foregoing detailed disclosure is intended to be presented merely by way of example and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" may mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily referring to the same embodiment. Furthermore, the particular features, structures or characteristics may be combined as suitable in one or more embodiments of the present disclosure.

Further, it may be appreciated by those skilled in the art that aspects of the present disclosure may be illustrated and described herein in any of a count of patentable classes or contexts including any new and useful process, machine, manufacture, or composition of matter, or any new and useful improvement thereof. Accordingly, aspects of the present disclosure may be implemented entirely on hardware, entirely on software (including firmware, resident software, micro-code, etc.) or combining software and hardware. Furthermore, aspects of the present disclosure may take the form of a computer program product having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, etc., or any suitable combination thereof. A computer readable signal medium may be any computer readable medium that is able to communicate, propagate, or transport a program for use by or in connection with an instruction execution system, apparatus, or device. The program code embodied on the computer readable signal medium may be transmitted using any appropriate medium, including wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python etc., conventional procedural programming languages, such as the C programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of counts, letters, or other designations, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the counts expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the count of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/etc., referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

What is claimed is:

1. A method for generating a medical data processing network, wherein the method is performed by a medical imaging system including a medical imaging device, a processing device, a storage device, and one or more terminals, and the method comprises:

in response to receiving a training instruction, obtaining, by the processing device, first medical data in real time in case of changes in a clinical application environment, the training instruction being triggered by a user on an application interface of the processing device or the one or more terminals of the medical imaging system;

obtaining, by the processing device, a second network by training a first network based on the first medical data, wherein the first network and the second network are machine learning models, the training includes an unsupervised training, and the training the first network based on the first medical data includes:

training, by the processing device, the first network at a preset training frequency, wherein the preset training frequency is correlated to a daily scanning volume of the medical imaging device;

generating, by the processing device, a test result by inputting second medical data into the second network, the second medical data including a test sample set;

determining, by the processing device, an evaluation result of a performance of the second network based on the test result; and in response to the evaluation result indicating that the performance of the second network satisfies a requirement, storing, by the processing device, a parameter of the second network in the storage device.

2. The method of claim 1, wherein the obtaining a second network by training a first network based on the first medical data includes:

automatically generating training data and a label based on the first medical data; and obtaining the second network by training the first network based on the training data and the label.

3. The method of claim 1, wherein the first network is used for a reconstruction of the first medical data, the first network is implemented based on a diffusion model, and the training the first network based on the first medical data includes:

generating an intermediate image by reconstructing the first medical data using a preset algorithm; and training the first network based on the intermediate image.

4. The method of claim 3, wherein the training the first network based on the intermediate image includes:

training, by adding image quality interference information to the intermediate image, the first network based on the intermediate image.

5. The method of claim 4, wherein the training, by adding the image quality interference information to the intermediate image, the first network based on the intermediate image includes:

iteratively updating the first network until a preset termination condition is satisfied, wherein each round of the iterative update includes:

generating a noise sample;

generating a sample intermediate image by adding the noise sample to the intermediate image;

obtaining a noise prediction value based on the sample intermediate image through the first network;

determining a first parameter based on the noise sample and the noise prediction value;

determining a second parameter based on the intermediate image; and updating the parameter of the first network based on the first parameter and the second parameter.

6. The method of claim 5, wherein the generating a noise sample includes selecting a noise distribution from a noise distribution set as the noise sample, wherein the noise distribution is a Gaussian distribution or a Poisson distribution, and the noise distribution set is determined by:

determining a generation parameter of the noise distribution set based on a function and a network complexity of the first network, the generation parameter at least including a size of the noise distribution set; and forming the noise distribution set by obtaining a certain count of noise distributions according to the generation parameter.

7. The method of claim 4, wherein the training, by adding the image quality interference information to the intermediate image, the first network based on the intermediate image includes:

obtaining a denoised image by performing a denoising on the intermediate image; and training the first network based on the denoised image.

8. The method of claim 1, wherein the method further includes:

presenting the test result on the application interface.

9. The method of claim 8, wherein in response to receiving a confirmation instruction, determining that the evaluation result indicates that the performance of the second network satisfies the requirement, the confirmation instruction being triggered by the user on the application interface; and in response to receiving a re-training instruction, determining that the evaluation result indicates that the performance of the second network does not satisfy the requirement, the re-training instruction being triggered by the user on the application interface.

10. The method of claim 1, wherein the method further includes:

in response to that the evaluation result indicates that the performance of the second network does not satisfy the requirement, re-obtaining new first medical data;

obtaining a third network based on the new first medical data by training the second network; and generating a test result by inputting the second medical data into the third network; and determining an evaluation result of a performance of the third network based on the test result of the third network until the evaluation result of the third network indicates that the performance of the third network satisfies the requirement.

11. The method of claim 1, wherein the obtaining first medical data includes:

obtaining initial medical data;

determining whether the initial medical data satisfies a preset training condition, the preset training condition including at least one of whether a count of the initial medical data reaches a preset count threshold, whether the initial medical data is accurate, or whether a size of the initial medical data satisfies a preset size threshold;

in response to that the initial medical data satisfies the preset training condition, designating the initial medical data as the first medical data; and in response to that the initial medical data does not satisfy the preset training condition, obtaining new initial medical data and repeatedly determining whether the new initial medical data satisfies the preset training condition until the new initial medical data that satisfies the preset training condition is obtained.

12. The method of claim 11, wherein the preset count threshold is correlated with at least one of function of the first network or a training progress of the first network.

13. The method of claim 1, wherein the storing a parameter of the second network includes:

obtaining a labeled parameter by labeling the parameter of the second network, the labeling being related to at least one of a function and a type of the second network; and storing the labeled parameter.

14. The method of claim 1, further comprising:

syncing or sharing the preset training frequency across a plurality of medical centers associated with the medical data processing network to make training frequencies of the plurality of medical centers identical.

15. The method of claim 14, wherein the method is performed during a spare time when the medical imaging device is not performing a scan.

16. The method of claim 15, wherein the preset training frequency is determined by using a vector database based on imaging data of the medical imaging device, and the vector database includes reference vectors of the imaging data corresponding to a plurality of daily scanning volumes and reference training frequencies corresponding to the reference vectors.

17. The method of claim 16, wherein the preset training frequency is determined by:

constructing, by the processing device, a target feature vector based on the daily scanning volume of the medical imaging device;

matching, by the processing device, at least one reference vector in the vector database that satisfies a preset condition based on the target feature vector, wherein the preset condition includes a distance between the target feature vector and each of the at least one reference vector is less than a distance threshold; and taking, by the processing device, an average value of reference training frequencies corresponding to the at least one reference vector as the preset training frequency.

18. A medical imaging system including a medical imaging device, a processing device, a storage device, one or more terminals, and a network; wherein the processing device is configured to:

in response to receiving a training instruction, obtain first medical data in real time in case of changes in a clinical application environment, the training instruction being triggered by a user on an application interface of the processing device or the one or more terminals of the medical imaging system;

obtain a second network by training a first network based on the first medical data, wherein the first network and the second network are machine learning models, the training includes an unsupervised training, and the training the first network based on the first medical data includes:

training the first network at a preset training frequency, wherein the preset training frequency is correlated to a daily scanning volume of the medical imaging device;

generate a test result by inputting second medical data into the second network, the second medical data including a test sample set;

determine an evaluation result of a performance of the second network based on the test result; and in response to the evaluation result indicating that the performance of the second network satisfies a requirement, store a parameter of the second network in the storage device.

19. A method for processing medical data, wherein the method is performed on a medical imaging system including a medical imaging device, a processing device, a storage device, and one or more terminals, and the method comprises:

obtaining, by the processing device, medical data to be processed from the medical imaging device;

in response to receiving a selection instruction, obtaining, by the processing device, a basic network model and a target parameter, wherein the selection instruction is triggered by a user on an application interface of the processing device or the one or more terminals, and the selection instruction is configured to select the target parameter from a plurality of parameters stored in the storage device and the basic network model from a plurality of network models stored in the storage device;

generating a target network model based on the target parameter and the basic network model, wherein the target network model and the basic network model are machine learning models; and obtaining a processing result by inputting the medical data to be processed into the target network model, wherein the processing result includes a processed medical data.

20. The method of claim 19, wherein the plurality of parameters are generated in the medical imaging system by:

in response to receiving a training instruction, obtaining, by the processing device, first medical data in real time in case of changes in a clinical application environment, the training instruction being triggered by the user on the application interface of the processing device or the one or more terminals of the medical imaging system;

obtaining, by the processing device, a second network by training a first network based on the first medical data, wherein the training includes an unsupervised training, and the training the first network based on the first medical data includes:

training the first network at a preset training frequency, wherein the preset training frequency is correlated to a daily scanning volume of the medical imaging device;

generating, by the processing device, a test result by inputting second medical data into the second network, the second medical data including a test sample set;

determining, by the processing device, an evaluation result of a performance of the second network based on the test result; and in response to the evaluation result indicating that the performance of the second network satisfies a requirement, designating, by the processing device, a parameter of the second network as one of the plurality of parameters.

* * * * *